United States Patent [19]

Takematsu et al.

[11] Patent Number: 4,826,859

[45] Date of Patent: May 2, 1989

[54] FUNGICIDAL METHODS CONTAINING N-PYRIDYLCARBAMATES

[75] Inventors: Tetsuo Takematsu, Tochigi; Yuji Nonaka, Yamaguchi; Akira Nakanishi, Yamaguchi; Hideo Morinaka, Yamaguchi, all of Japan

[73] Assignee: Tosoh Corporation, Yamaguchi, Japan

[21] Appl. No.: 838,500

[22] Filed: Mar. 11, 1986

[30] Foreign Application Priority Data

Mar. 11, 1985 [JP] Japan .................................. 60-46474

[51] Int. Cl.$^4$ ............................................. A01N 43/30
[52] U.S. Cl. .................... 514/349; 514/312; 514/352
[58] Field of Search .................... 514/312, 352, 349

[56] References Cited

U.S. PATENT DOCUMENTS

| | | | |
|---|---|---|---|
| 3,969,362 | 7/1976 | Takahashi et al. | 260/295 |
| 4,228,181 | 10/1980 | Grotkopp et al. | 514/480 |
| 4,551,169 | 11/1985 | Takematsu et al. | 71/94 |
| 4,554,012 | 11/1985 | Takematsu et al. | 71/92 |

FOREIGN PATENT DOCUMENTS

| | | |
|---|---|---|
| 0000934 | 3/1979 | European Pat. Off. . |
| 0090263 | 10/1983 | European Pat. Off. . |
| 0144570 | 7/1985 | European Pat. Off. . |
| 0058916 | 4/1985 | Japan .................................. 514/352 |
| 2124617 | 2/1984 | United Kingdom . |
| 2138804 | 10/1984 | United Kingdom . |

*Primary Examiner*—Leonard Schenkman
*Attorney, Agent, or Firm*—Sughrue, Mion, Zinn, Macpeak & Seas

[57] ABSTRACT

Fungicidal composition comprising a fungicidally effective amount of the N-pyridylcarbamate derivative having the formula (I) as an active ingredient:

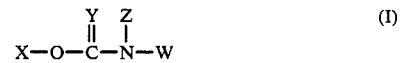

wherein X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4,-tetrahydro-6-naphthyl, 2-quinolyl, or a phenyl group having one or two of the same or different substituents selected from the group of halogen atom, lower alkyl, lower alkenyl, lower alkoxy, lower alkenyloxy, halogenated lower alkyl, lower alkylthio, lower alkyl-sulfonyl, lower alkylamino, nitro, and methylenedioxy; Y is an oxygen atom or a sulfur atom; Z is lower alkyl group; W is pyridyl group having one or two of the same substituents selected from the group of lower alkyl, lower alkoxy, lower alkenyloxy, and lower alkylamino, and biologically inert carriers has excellent fungicidal activity against a variety of molds, and can be used to protect plants from fungal infections.

7 Claims, No Drawings

FUNGICIDAL METHODS CONTAINING N-PYRIDYLCARBAMATES

BACKGROUND OF THE INVENTION

1. Field of the Invention

This invention relates to fungicidal composition comprising an N-pyridylcarbamate derivative as an active ingredient.

2. Description of Prior Art

There are many fungicide which are generally in wide use and contribute to crop protection and increasing crop yield. However, the development of new agricultural fungicides having excellent fungicidal effects and correspondingly high practical values has been a matter of great importance.

Some of the present inventors and other persons had previously found that specific N-pyridylcarbamate derivatives have herbicidal activity and can be used as herbicides, and disclosed the corresponding N-pyridylcarbamate derivatives in U.S. Pat. No. 4,554,012 and European Patent specification No. 0090263 B1. Further, it was also previously found that said derivatives have antifungal activity and can be used as antifungal agents. In European Patent Application No. 0144570 A2, "antifungal composition" was disclosed.

DESCRIPTION OF THE INVENTION

The present invention is to provide fungicidal composition for agriculture having excellent fungicidal activity against a wide variety of molds and accordingly a high practical value.

PREFERRED EMBODIMENT OF THE INVENTION

The present invention provides fungicidal composition (hereinafter referred to as the present composition) which comprises (1) a biologically inert carrier, (2) an effective amount of an N-pyridylcarbamate derivative having the following formula (I) as an active ingredient.

$$X-O-\overset{\overset{Y}{\|}}{C}-\overset{\overset{Z}{|}}{N}-W \quad (I)$$

wherein X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4,-tetrahydro-6-naphthyl, 2-quinolyl, or a phenyl group having one or two of the same or different substituents selected from the group of halogen atom, lower alkyl, lower alkenyl, lower alkoxy, lower alkenyloxy, halogenated lower alkyl, lower alkylthio, lower alkyl-sulfonyl, lower alkylamino, nitro, and methylenedioxy; Y is an oxygen atom or a sulfur atom; Z is lower alkyl group; W is pyridyl group having one or two of the same substituents selected from the group of lower alkyl, lower alkoxy, lower alkenyloxy, and lower alkylamino; and if desired, (3) a suitable adjuvant.

The N-pyridylcarbamate derivatives represented by the formula (I), which is the active ingredient of the present composition, can be produced in accordance with the following reaction schemes.

$$X-OH + Hal-\overset{\overset{Y}{\|}}{C}-\overset{\overset{Z}{|}}{N}-W \longrightarrow X-O-\overset{\overset{Y}{\|}}{C}-\overset{\overset{Z}{|}}{N}-W \quad (I)\ldots(1)$$

$$X-O-\overset{\overset{Y}{\|}}{C}-Hal + HN-\overset{\overset{Z}{|}}{W} \longrightarrow X-O-\overset{\overset{Y}{\|}}{C}-\overset{\overset{Z}{|}}{N}-W \quad (I)\ldots(2)$$

wherein X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4,-tetrahydro-6-naphthyl, 2-quinolyl, or a phenyl group having one or two of the same or different substituents selected from the group of halogen atoms, lower alkyl, lower alkenyl, lower alkoxy, lower alkenyloxy, halogenated lower alkyl, lower alkylthio, lower alkyl-sulfonyl, lower alkylamino, nitro, and methylenedioxy; Y is an oxygen atom or a sulfur atom; Z is lower alkyl group; W is pyridyl group having one or two of the same substituents selected from the group of lower alkyl, lower alkoxy, lower alkenyloxy, and lower alkylamino; Hal is a halogen atom.

The above reactions proceed in the presence of dehydrohalogenation agents, and further in the presence or absence of a reaction solvent, usually at a reaction temperature of 0° to 150° C. during the reaction time from about several minutes to 48 hours.

The dehydrohalogenation agents include alkali metal hydroxides such as sodium hydroxide, potassium hydroxide, and the like, alkaline earth metal hydroxide such as calcium hydroxide, and the like, alkali metal carbonates such as sodium carbonate, potassium carbonate, sodium hydrogen carbonate, potassium hydrogen carbonate, and the like, metal hydrides such as sodium hydride, and the like, tertiary amines such as triethylamine, dimethylaniline, pyridine, and the like. In the reaction scheme (2), the starting aminopyridine derivative may be used as a dehydrohalogenation agent.

Reaction solvents to be used in the reaction represented by schemes (1) and (2) include water, alcoholes such as methanol, ethanol, isopropanol, and the like, ketones such as aceton, methylethylketone, and the like, aromatic hydrocarbons such as benzene, toluene, xylene, and the like, ethers such as ethyl ether, tetrahydrofuran, dioxane, and the like, halogenated hydrocarbons such as chlorobenzene, chloroform, carbon tetrachloride, dichloroethane, and the like, polar solvents such as dimethylformamide, dimethylsulfoxide, and the like.

The process for producing the N-pyridylcarbamate derivatives represented by the formula (I) as an active ingredient of the present composition will be explained in detail with reference to particular examples.

EXAMPLE OF SYNTHESIS 1

Synthesis of O-4-bromo-3-ethylphenyl N-(6-methoxy-2-pyridyl)-N-methyl-thiocarbamate (Compound No. 5)

To a mixture of 1.38 g of 2-methoxy-6-methylaminopyridine and 1.38 g of anhydrous potassium carbonate in 20 ml of acetone was added dropwise 2.80 g of O-4-bromo-3-ethylphenyl chlorothioformate in 20 ml of acetone under stirring at room temperature. The resulting mixture was stirred for 30 minutes at room temperature, and then subjected to refluxing for 2 hours. After the reaction mixture was cooled to room temperature, inorganic salts were removed by filtration and acetone was removed by distillation. The residue was purified by column chromatography (silica gel, benzene) to obtain 2.78 g of title compound. A part of product was recrystallized from benzene-hexane to give colorless crystal having a melting point of 84°–85° C.

Elemental Analysis: Found (%): C 50.46, H 4.31, N 7.03. Calcd. (%): C 50.40, H 4.49, N 7.34.

EXAMPLE OF SYNTHESIS 2

Synthesis of 3-t-butyl-4-chlorophenyl N-(6-methoxy-2-pyridyl)-N-methylcarbamate (Compound No. 56)

A mixture of 2.01 g of N-(6-methoxy-2-pyridyl)-N-methylcarbamoyl chloride, 1.85 g of 3-t-butyl-4-chlorophenyl, and 1.38 g of anhydrous potassium carbonate in 30 ml of acetone was refluxed under heating for 24 hours. After the reaction mixture was cooled to room temperature, inorganic salts were removed by filtration and then acetone was removed by distillation under reduced pressure. The residue was purified by the column chromatography (silica gel, benzene) to obtain 3.13 g of title compound. A part of product was recrystallized from hexane to give a colorless crystal having a melting point of 54°–56° C.

Elemental Analysis Found (%): C 62.04, H 5.95, N 7.74. Calcd. (%): C 61.97, H 6.06, N 8.03.

In a similar manner as that used in Examples of syntheses 1 and 2, the N-pyridylcarbamate derivatives represented by the formula (I) as an active ingredient of the present composition were synthesized. Typical examples of these carbamates, together with their physical properties are shown below, but the active ingredient of the fungicidal composition of the present invention is not at all limited to these listed compounds.

These compounds will be referred to by their compound number in the descriptions.

| Compound No. | Compound | Physical Property |
|---|---|---|
| 1 | 2-Naphthyl N—methyl-N—(4-methyl-2-pyridyl)carbamate | $n_D^{25}$ 1.6191 |
| 2 | O—2-Naphthyl N—methyl-N—(6-methyl-2-pyridyl)thiocarbamate | m.p. 149.5–150.5° C. |
| 3 | O—2-Naphthyl N—methyl-N—(5-methyl-2-pyridyl)thiocarbamate | m.p. 122.5–124.5° C. |
| 4 | O—2-Naphthyl N—methyl-N—(4-methyl-2-pyridyl)thiocarbamate | m.p. 107–108.5° C. |
| 5 | O—4-Bromo-3-ethylphenyl N—(6-methoxy-2-pyridyl)-N—methylthiocarbamate | m.p. 84–85° C. |
| 6 | 2-Naphthyl N—methyl-N—(6-methoxy-2-pyridyl)carbamate | m.p. 140.5–142° C. |
| 7 | O—2-Naphthyl N—methyl-N—(6-methoxy-2-pyridyl)thiocarbamate | m.p. 95.5–97° C. |
| 8 | O—5,6,7,8-Tetrahydro-2-naphthyl N—methyl-N—(6-methyl-2-pyridyl)thiocarbamate | m.p. 137.5–139° C. |
| 9 | O—5-Indanyl N—methyl-N—(4-methyl-2-phridyl)thiocarbamate | m.p. 93.5–95° C. |
| 10 | O—5-Indanyl N—(6-methoxy-2-pyridyl)-N—methylthiocarbamate | m.p. 95–96° C. |
| 11 | O—5,6,7,8-Tetrahydro-2-naphthyl N—(6-methoxy-2-pyridyl)-N—methyl-thiocarbamate | m.p. 98.5–99.5° C. |
| 12 | O—1,4-Methano-1,2,3,4-tetrahydro-6-naphthyl N—(6-methoxy-2-pyridyl)-N—methylthiocarbamate | m.p. 91–93° C. |
| 13 | 1,4-Methano-1,2,3,4-tetrahydro-6-naphthyl N—(6-methoxy-2-pyridyl)-N—methylthiocarbamate | m.p. 60.5–62° C. |
| 14 | O—2-Naphthyl N—methyl-N—(4,6-dimethyl-2-pyridyl)thiocarbamate | m.p. 117–119° C. |
| 15 | O—5-Indanyl N—methyl-N—(4,6-dimethyl-2-pyridyl)thiocarbamate | m.p. 128–129° C. |
| 16 | O—4-t-Butylphenyl N—(6-methoxy-2-pyridyl)-N—methylthiocarbamate | m.p. 87–88° C. |
| 17 | O—2-Naphthyl N—(6-ethoxy-2-pyridyl)-N—methylthiocarbamate | m.p. 90.5–91° C. |
| 18 | O—4-t-Butylphenyl N—methyl-N—(6-methyl-2-pyridyl)thiocarbamate | m.p. 127–128.5° C. |
| 19 | O—4-t-Pentylphenyl N—(6-methoxy-2-pyridyl)-N—methylthiocarbamate | m.p. 113–114.5° C. |
| 20 | O—5,6,7,8-Tetrahydro-2-naphthyl N—(6-allyloxy-2-pyridyl)-N—methylthiocarbamate | m.p. 88–89° C. |
| 21 | O—1,4-Ethano-1,2,3,4-tetrahydro-6-naphthyl N—(6-methoxy-2-pyridyl)-N—methylthiocarbamate | m.p. 125–126.5° C. |
| 22 | O—3,4-Dimethylphenyl N—(6-methoxy-2-pyridyl)-N—methylthiocarbamate | m.p. 111–112° C. |
| 23 | O—5,6,7,8-Tetrahydro-2-naphthyl N—(6-dimethylamino-2-pyridyl)-N—methylthiocarbamate | m.p. 108–109.5° C. |
| 24 | O—2-Naphthyl N—(6-ethyl-2-pyridyl)-N—methylthiocarbamate | m.p. 107–108° C. |
| 25 | O—2-Naphthyl N—methyl-N—(5,6-dimethyl-2-pyridyl)thiocarbamate | m.p. 108–109° C. |
| 26 | O—5-Indanyl N—methyl-N—(5,6-dimethyl-2-pyridyl)thiocarbamate | m.p. 102.5–104° C. |
| 27 | O—5,6,7,8-Tetrahydro-2-naphthyl N—methyl-N—(5,6-dimethyl-2-pyridyl)thiocarbamate | m.p. 98–99.5° C. |
| 28 | O—3-t-Butylphenyl N—(6-methoxy-2-pyridyl)-N—methylthiocarbamate | m.p. 85.5–86.5° C. |
| 29 | O—4-s-Buthylphenyl N—(6-methoxy-2-pyridyl)-N—methylthiocarbamate | m.p. 52–53° C. |
| 30 | O—4-Isopropylphenyl N—(6-methoxy-2-pyridyl)-N—methylthiocarbamate | m.p. 55–56° C. |
| 31 | O—3-Methylphenyl N—(6-methoxy-2-pyridyl)-N—methylthiocarbamate | $n_D^{25}$ 1.6070 |
| 32 | O—3-Ethylphenyl N—(6-methoxy-2-pyridyl)-N—methylthiocarbamate | $n_D^{25}$ 1.6019 |
| 33 | O—4-Ethylphenyl N—(6-methoxy-2-pyridyl)-N—methylthiocarbamate | m.p. 69.5–70.5° C. |
| 34 | O—4-Bromophenyl N—(6-methoxy-2-pyridyl)-N—methylthiocarbamate | m.p. 87–88° C. |
| 35 | O—2-Naphthyl N—methyl-N—(6-dimethylamino-2-pyridyl)thiocarbamate | m.p. 135–136° C. |
| 36 | O—4-t-Butylphenyl N—methyl-N—(6-dimethylamino-2-pyridyl)thiocarbamate | m.p. 89.5–90.5° C. |
| 37 | O—3-t-Butylphenyl N—methyl-N—(6-methyl-2-pyridyl)thiocarbamate | m.p. 116–117.5° C. |
| 38 | O—4-Chloro-3-methylphenyl N—(6-methoxy-2-pyridyl)-N—methylthiocarbamate | m.p. 93–94° C. |
| 39 | O—4-Ethyl-3-methylphenyl N—(6-methoxy-2-pyridyl)-N—methylthiocarbamate | m.p. 83–85° C. |
| 40 | O—5-Isopropyl-2-methylphenyl N—(6-methoxy-2-pyridyl)-N—methylthiocarbamate | $n_D^{25}$ 1.5814 |
| 41 | O—4-Isopropyl-3-methylphenyl N—(6-methoxy-2-pyridyl)-N—methylthiocarbamate | m.p. 67–68° C. |
| 42 | O—4-t-Butyl-3-methylphenyl N—(6-methoxy-2-pyridyl)-N—methylthiocarbamate | m.p. 97–98° C. |
| 43 | O—4-Trifluoromethylphenyl N—(6-methoxy-2-pyridyl)-N—methylthiocarbamate | m.p. 81–82° C. |
| 44 | O—4-Nitrophenyl N—(6-methoxy-2-pyridyl)-N—methylthiocarbamate | m.p. 91–92.5° C. |

| Compound No. | Compound | Physical Property |
|---|---|---|
| 45 | O—3-Chloro-4-methylphenyl N—(6-methoxy-2-pyridyl)-N—methylthiocarbamate | m.p. 103–105° C. |
| 46 | O—4-Bromo-3-methylphenyl N—(6-methoxy-2-pyridyl)-N—methylthiocarbamate | m.p. 105.5–107° C. |
| 47 | O—3-Trifluoromethylphenyl N—(6-methoxy-2-pyridyl)-N—methylthiocarbamate | m.p. 71–72° C. |
| 48 | O—3-Isopropylphenyl N—(6-methoxy-2-pyridyl)-N—methylthiocarbamate | m.p. 50–51° C. |
| 49 | O—3-Bromophenyl N—(6-methoxy-2-pyridyl)-N—methylthiocarbamate | m.p. 69–69.5° C. |
| 50 | O—3,4-Dichlorophenyl N—(6-methoxy-2-pyridyl)-N—methylthiocarbamate | m.p. 78–79° C. |
| 51 | O—4-Chloro-3-methylphenyl N—methyl-N—(6-methyl-2-pyridyl)thiocarbamate | m.p. 134–136° C. |
| 52 | O—3,4-Dimethylphenyl N—methyl-N—(4-methyl-2-pyridyl)thiocarbamate | m.p. 113–114° C. |
| 53 | O—4-Methylphenyl N—(6-methoxy-2-pyridyl)-N—methylthiocarbamate | m.p. 66.5–67.5° C. |
| 54 | O—4-Chloro-3-methoxyphenyl N—(6-methoxy-2-pyridyl)-N—methylthiocarbamate | m.p. 64.5–65.5° C. |
| 55 | O—4-Chloro-3-allyloxyphenyl N—(6-methoxy-2-pyridyl)-N—methylthiocarbamate | m.p. 116.5–117.5° C. |
| 56 | 3-t-Butyl-4-chlorophenyl N—(6-methoxy-2-pyridyl)-N—methylcarbamate | m.p. 54–56° C. |
| 57 | O—3-t-Butylphenyl N—methyl-N—(6-dimethylamino-2-pyridyl)thiocarbamate | $n_D^{25}$ 1.6002 |
| 58 | O—4-t-Butylphenyl N—methyl-N—(6-methylamino-2-pyridyl)thiocarbamate | m.p. 113–114° C. |
| 59 | O—3-t-Butylphenyl N—methyl-N—(6-methylamino-2-pyridyl)thiocarbamate | m.p. 73–74° C. |
| 60 | O—4-Methoxyphenyl N—(6-methoxy-2-pyridyl)-N—methylthiocarbamate | m.p. 97.5–98.5° C. |
| 61 | O—4-Ethoxyphenyl N—(6-methoxy-2-pyridyl)-N—methylthiocarbamate | m.p. 96.5–97.5° C. |
| 62 | O—4-Methylthiophenyl N—(6-methoxy-2-pyridyl)-N—methylthiocarbamate | m.p. 106.5–108° C. |
| 63 | O—3,4-Methylenedioxyphenyl N—(6-methoxy-2-pyridyl)-N—methylthiocarbamate | m.p. 102.5–103.5° C. |
| 64 | O—5,6,7,8-Tetrahydro-2-naphthyl N—ethyl-N—(6-methoxy-2-pyridyl)thiocarbamate | $n_D^{25}$ 1.6030 |
| 65 | O—4-Propylphenyl N—(6-methoxy-2-pyridyl)-N—methylthiocarbamate | m.p. 40–42° C. |
| 66 | O—3-Methyl-4-nitrophenyl N—(6-methoxy-2-pyridyl)-N—methylthiocarbamate | m.p. 59–61° C. |
| 67 | O—3-Methyl-4-methylthiophenyl N—(6-methoxy-2-pyridyl)-N—methylthiocarbamate | m.p. 78–79° C. |
| 68 | O—4-Trifluoromethylphenyl N—(6-dimethylamino-2-pyridyl)-N—methylthiocarbamate | m.p. 74–76° C. |
| 69 | O—3-Dimethylaminophenyl N—(6-methoxy-2-pyridyl)-N—methylthiocarbamate | m.p. 111–113° C. |
| 70 | O—4-Methylsulfonylphenyl N—(6-methoxy-2-pyridyl)-N—methylthiocarbamate | m.p. 121–122° C. |
| 71 | O—4-Chloro-3-ethylphenyl N—(6-methoxy-2-pyridyl)-N—methylthiocarbamate | m.p. 69.5–70.5° C. |
| 72 | O—4-Bromo-3-isopropylphenyl N—(6-methoxy-2-pyridyl)-N—methylthiocarbamate | m.p. 82–84° C. |
| 73 | O—4-Bromo-3-t-butylphenyl N—(6-methoxy-2-pyridyl)-N—methylthiocarbamate | m.p. 117–119° C. |
| 74 | O—2-Quinolyl N—(6-methoxy-2-pyridyl)-N—methylthiocarbamate | m.p. 106–108° C. |
| 75 | O—2-Naphthyl N—methyl-N—(3-methyl-2-pyridyl)thiocarbamate | m.p. 127–129° C. |
| 76 | O—2-Naphthyl N—(4-ethyl-2-pyridyl)-N—methylthiocarbamate | m.p. 99.5–101° C. |
| 77 | O—4-Isopropenylphenyl N—(6-methoxy-2-pyridyl)-N—methylthiocarbamate | m.p. 93–93.5° C. |

The present composition comprising an N-pyridylcarbamate derivative represented by the formula (I) as the active ingredient, having excellent fungicidal activity against a variety of molds, can be used for elimination of pathogenic fungi propagating in plants.

The N-pyridylcarbamate derivative represented by the formula (I) can be applied as it is, without being mixed with other ingredients but is ordinarily applied in a mixture with a carrier for easier use as a fungicide. The form of application includes formulations such as a powder, a wettable powder, an oil solution, an emulsifiable concentrate, a tablet, a granule, a microgranule, an aerosol, a flowable and the like.

These formulations contain 0.1 to 99.9% by weight, preferably 1 to 99% by weight of an N-pyridylcarbamate derivatives represented by the formula (I) as the active ingredient.

The solid carrier includes fine powders or particles of kaolin clay, attapulgite clay, bentonite, acid clay, pyrophyllite, talc, diatomaceous earth, calcite, corn stem powder, walnut shell powder, urea, ammonium sulfate, synthetic hydrous silicon oxide, etc. The liquid carrier includes aromatic hydrocarbons such as toluene, xylene, and the like, alcohols such as isopropanol, ethylene glycol, 2-butoxyethanol, and the like, ketones such as acetone, cyclohexanone, isophorone, and the like, vegetable oils such as soybean oil, cotton seed oil, and the like, mineral oil, kerosine, dimethyl sulfoxide, acetonitrile, water, etc.

The surfactant used for emulsification, dispersion, spreading, etc. includes anionic surfactants such as an alkyl (aryl) sulfonate, a dialkyl sulfosuccinate, a polyoxyethylene alkyl aryl ether phosphoric ester salt, an alkylsulfonic ester, a naphthalenesulfonic acid - formalin condensate and the like; non-ionic surfactants such as a polyoxyethylene alkyl ether, a polyoxyethylene, polyoxypropylene block copolymer, a sorbitan fatty acid ester, and the like. The adjuvant includes a ligninsulfonic acid salt, an dalginic acid salt, a polyvinyl alcohol, gum arabic, a carboxymethyl cellulose, isopropyl phosphoric acid, etc.

As the fungi which can be exterminated by the present fungicide, there can be mentioned, for example, *Piricularia oryzae, Pellicularia filamentosa, Podosphaera leoucotricha, Phyllactinia kakicola, Uncinula necator, Erysiphe graminis, Sphaerotheca fuliginea, Sphoerotheca humili, Botrytis cinerea, Venturia inaequalis, Cladosporium cucumerium, Marssonia mali, Cercospora beticola,*

Cercospora arachidicola, Sclerotinia cinerea, Penicillium italicum, Penicillium digitatum, Cercosphoridium personatum, Septoria nodorum, and Altenaria solani.

In addition, the fungicidal composition of the present invention can be applied after incorporating them with other agricultural chemicals used in the same field, for example, herbicides, insecticides, fungicides, plant growth regulators or fertilizers.

The present invention will be explained in more detail below by way of Examples. Parts and % refer to parts by weight and % by weight, respectively.

EXAMPLE 1

Preparation of powder

Two parts of the compound No. 77, 88 parts of clay and 10 parts of talc were ground and mixed thoroughly to obtain a powder containing 2% of the active ingredient.

EXAMPLE 2

Preparation of wettable powder

Thirty parts of the compound No. 76, 45 parts of diatomaceous earth, 20 parts of white carbon, 3 parts of Emal powder (Trade Name, manufactured by Kao Atlas Co., Ltd.) and 2 parts of San Ekisu P201 (Trade Name, manufactured by San-yo Kokusaku Pulp Co., Ltd.) were ground and mixed thoroughly to obtain a wettable powder containing 30% of the active ingredient.

EXAMPLE 3

Preparation of wettable powder

Fifty parts of the compound No. 75, 45 parts of diatomaceous earth, 2.5 parts of Neopelex powder (Trade Name, manufactured by Kao Atlas Co. Ltd.) and 2.5 parts of San Ekisu P201 were ground and mixed thoroughly to obtain a wettable powder containing 50% of the active ingredient.

EXAMPLE 4

Preparation of emulsifiable concentrate

Ten parts of the compound No. 71, 80 parts of cyclohexanone and 10 parts of Nonipol 100 (Trade Name, manufactured by San-yo Kasei Kogyo Co., Ltd.) were mixed to obtain an emulsifiable concentrate containing 10% of the active ingredient.

EXAMPLE 5

Test of fungicidal effect on rice blast (assay for young seedling)

On 2.2 to 2.5 leaf stage of rice plant (variety: Nihonbare) grown in a 1/5,000 are pot was sprayed a dispersed solution of wettable powder, which was prepared in accordance with Example 3, containing 200 ppm of an active ingredient, in a proportion of 150 liters per 10 are, using a spray gun. After rice plant had been air-dried, a suspension of spores of Piricularia oryzae was sprayed on the rice plant for inoculation. After 10 days from the spraying of the spore suspension, the condition of infection of the third leaves (20 leaves) was examined on all seedlings. The incidence and preventive value were calculated using the following equation. The test results are shown in Table 1.

$$\text{Incidence (\%)} = \frac{3n_3 + 2n_2 + n_1}{3 \times (\text{number of leaves examined})} \times 100$$

$n_3$: Number of leaves whose stigma area is 51 to 100% of the total leaf area.

$n_2$: Number of leaves whose stigma area is 26 to 50% of the total leaf area.

$n_1$: Number of leaves whose stigma area is 1 to 25% of the total leaf area.

$$\text{Preventive value (\%)} = \frac{t_o - t}{t_o} \times 100$$

t: Incidence of treated seedlings
$t_o$: Incidence of untreated seedlings.

TABLE 1

Test results of fungicidal effect on rice blast

| Active ingredient Compound No. | Phytotoxicity | Incidence (%) | Preventive value (%) |
|---|---|---|---|
| 2 | None | 28.0 | 34.9 |
| 8 | None | 27.3 | 36.5 |
| 15 | None | 29.7 | 30.9 |
| 21 | None | 29.7 | 30.9 |
| 34 | None | 29.3 | 31.9 |
| 47 | None | 26.0 | 39.5 |
| 50 | None | 24.0 | 44.2 |
| 61 | None | 24.0 | 44.2 |
| 69 | None | 28.0 | 34.9 |
| untreated | — | 43.0 | — |

EXAMPLE 6

Test of fungicidal effect on rice sheath blight

On 2.2 to 2.5 leaf stage of rice plant (variety: Nihonbare) grown in a 1/5,000 are pot was sprayed a dispersed solution of wettable powder, which was prepared in accordance with Example 3, containing 200 ppm of an active ingredient, in a proportion of 150 liters per 10 are, using a spray gun. After rice plant had been air-dried, Pellicularia filamentosa was inoculated to the soil surface portion of the rice plant. After the inoculation, the pot was covered with a thin polyvinylidene chloride film and placed in a wet room of 30° to 32° C. for infection. When the infection had appeared, the plastic film was removed and the pot was stored in a warm room of 25° to 30° C. On 10th day from the inoculation, the condition of infection was examined on all seedlings. The incidence and preventive value calculated in the same way as in Example 5. The test results are shown in Table 2.

TABLE 2

Test results of fungicidal effect on rice sheath blight

| Active ingredient Compound No. | Phytotoxicity | Incidence (%) | Preventive value (%) |
|---|---|---|---|
| 3 | None | 63.5 | 32.9 |
| 4 | None | 37.1 | 60.8 |
| 7 | None | 40.5 | 57.2 |
| 18 | None | 63.0 | 33.5 |
| 33 | None | 75.0 | 20.7 |
| 38 | None | 61.2 | 35.3 |
| 41 | None | 58.4 | 38.3 |
| 67 | None | 71.1 | 24.8 |
| untreated | — | 94.6 | — |

EXAMPLE 7

Test of fungicidal effect on cucumber gray mold (assay for fruit)

*Botrytis cinerea* was cultured in an agar medium in a Petri dish. When the fungus colonies spread to all the surface parts of the dish, a cucumber fruit treated with a dispersed solution of wettable powder, which was prepared in accordance with Example 3, containing 200 ppm of an active ingredient and then air-dried was placed on the colonies. Then, the dish was subjected to culture at 20° to 25° C. After 7 days, the discoloration area (change to brown) of the lower portion of this cucumber fruit was recorded. The incidence was calculated using the following equation. Preventive value was calculated as in Example 5. The test results are shown in Table 3.

$$\text{Incidence (\%)} = \frac{S}{S_o} \times 100$$

S: The discoloration area of the lower portion of the cucumber fruit $S_o$: The whole area of the lower portion of the cucumber fruit.

TABLE 3

Test results of fungicidal effect on cucumber

| Active ingredient Compound No. | Incidence (%) | Preventive value (%) |
|---|---|---|
| 5 | 4 | 95 |
| 23 | 1 | 99 |
| 56 | 1 | 99 |
| 71 | 3 | 96 |
| untreated | 85.0 | — |

EXAMPLE 8

Test of fungicidal effect on peanut blight

On peanut plant of 10–15 cm high was sprayed a dispersed solution of wettable powder, which was prepared in accordance with Example 3, containing 60 ppm of an active ingredient. After peanut plant had been air-dried, a suspension of condidiums of *Cercosposa arachidicola* was sprayed on the peanut plant for inoculation. After the inoculation, the peanut plant was placed under high relative humidity (about 80%) at about 21° C. for 72 hours and the plant was subjected to culture at room temperature. On 12 days from the inoculation, the condition of infection of the peanut plant was examined.

Incidence and preventive value calculated using the equations as in Example 5. The test results are shown in Table 4.

TABLE 4

Test results of fungicidal effect on peanut plant blight

| Active ingredient Compound No. | Incidence (%) | Preventive value (%) |
|---|---|---|
| 5 | 3 | 96 |
| 34 | 3 | 96 |
| 43 | 1 | 99 |
| untreated | 70 | — |

As is obvious from the above explanation, the present fungicide is sensitive to *Piricularia oryzae*, *Pellicularia filamentosa*, *Botrytis cinerea* and *Cercospora arachidicola* and is useful as an agricultural fungicide.

What is claimed is:

1. A method for protecting plants from fungal infections, comprising applying to said plants a fungicidally effective amount of an N-pyridylcarbamate derivative represented by the formula (I) as an active ingredient:

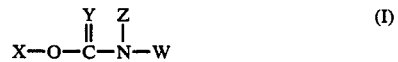

wherein X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or a phenyl group having one or two of the same or different substituents selected from the group of halogen atom, lower alkyl, lower alkenyl, lower alkoxy, lower alkenyloxy, halogenated lower alkyl, lower alkylthio, lower alkyl-sulfonyl, lower alkylamino, nitro, and methylenedioxy; Y is an oxygen atom or a sulfur atom; Z is lower alkyl group; W is pyridyl group having one or two of the same substituents selected from the group of lower alkyl, lower alkoxy, lower alkenyloxy, and lower alkylamino.

2. A method described in claim 1, wherein the N-pyridylcarbamate derivative is O-4-bromo-3-ethylphenyl N-(6-methoxy-2-pyridyl)-N-methylthiocarbamate.

3. A method described in claim 1, wherein the N-pyridylcarbamate derivative is O-5,6,7,8-tetrahydro-2-naphthyl N-(6-dimethylamino-2-pyridyl)-N-methylthiocarbamate.

4. A method described in claim 1, wherein the N-pyridylcarbamate derivative is O-4-bromophenyl N-(6-methoxy-2-pyridyl)-N-methylthiocarbamate.

5. A method described in claim 1, wherein the N-pyridylcarbamate derivative is O-4-trifluoromethyl N-(6-methoxy-2-pyridyl)-N-methylthiocarbamate.

6. A method described in claim 1, wherein the N-pyridylcarbamate derivative is 3-t-butyl-4-chlorophenyl N-(6-methoxy-2-pyridyl)-N-methylcarbamate.

7. A method described in claim 1, wherein the N-pyridylcarbamate derivative is O-4-chloro-3-ethylphenyl N-(6-methoxy-2-pyridyl)-N-methylthiocarbamate.

* * * * *